(12) United States Patent
Williams

(10) Patent No.: US 10,736,637 B2
(45) Date of Patent: Aug. 11, 2020

(54) BRAKE FOR ADAPTER ASSEMBLIES FOR SURGICAL DEVICES

(71) Applicant: Covidien LP, Mansfield, MA (US)

(72) Inventor: Justin Williams, Southbury, CT (US)

(73) Assignee: Covidien LP, Mansfield, MA (US)

(*) Notice: Subject to any disclaimer, the term of this patent is extended or adjusted under 35 U.S.C. 154(b) by 489 days.

(21) Appl. No.: 15/495,175

(22) Filed: Apr. 24, 2017

(65) Prior Publication Data

US 2017/0325816 A1    Nov. 16, 2017

Related U.S. Application Data

(60) Provisional application No. 62/334,013, filed on May 10, 2016.

(51) Int. Cl.
  *A61B 17/068*    (2006.01)
  *A61B 17/115*    (2006.01)
  (Continued)

(52) U.S. Cl.
  CPC ........ *A61B 17/1155* (2013.01); *A61B 17/068* (2013.01); *A61B 17/07207* (2013.01);
  (Continued)

(58) Field of Classification Search
  CPC ... A61B 17/115; A61B 17/072; A61B 17/068; A61B 2017/2901; A61B 2017/2902;
  (Continued)

(56) References Cited

U.S. PATENT DOCUMENTS 2,777,340 A    1/1957    Hettwer et al.
2,957,353 A    10/1960    Babacz
(Continued)

FOREIGN PATENT DOCUMENTS

CA    2451558 A1    1/2003
CN    1547454 A    11/2004
(Continued)

OTHER PUBLICATIONS

European Search Report dated Oct. 9, 2017, issued in EP Application No. 17170210.
(Continued)

*Primary Examiner* — Praachi M Pathak
(74) *Attorney, Agent, or Firm* — Carter, DeLuca & Farrell LLP

(57) ABSTRACT

An adapter assembly for operably connecting an end effector to an electromechanical surgical instrument includes a drive transfer assembly, a drive member, and a first pusher assembly. The drive transfer assembly includes first and second rotatable shafts. The drive member is operably connected to the first rotatable shaft for transferring rotational motion from the first rotatable shaft to effect a first function and the first pusher assembly is operably connected to the second rotatable shaft for converting rotational motion from the second rotatable shaft to longitudinal movement to effect a second function. The first pusher assembly includes a brake member for rotationally locking the drive member relative to the first pusher assembly.

19 Claims, 7 Drawing Sheets

(51) Int. Cl.
*A61B 17/072* (2006.01)
*A61B 90/00* (2016.01)
*A61B 17/00* (2006.01)
*A61B 17/29* (2006.01)

(52) U.S. Cl.
CPC ............... *A61B 2017/0046* (2013.01); *A61B 2017/00398* (2013.01); *A61B 2017/00473* (2013.01); *A61B 2017/00477* (2013.01); *A61B 2017/07278* (2013.01); *A61B 2017/2903* (2013.01); *A61B 2017/293* (2013.01); *A61B 2017/2929* (2013.01); *A61B 2090/034* (2016.02)

(58) Field of Classification Search
CPC .......... A61B 2017/00407; A61B 17/28; A61B 17/29; A61B 2017/2912; A61B 2017/292
USPC ..... 606/219, 139, 151, 45, 51, 52, 205–207, 606/142, 143; 227/175.1–182.1
See application file for complete search history.

(56) References Cited

U.S. PATENT DOCUMENTS

| | | | |
|---|---|---|---|
| 3,111,328 A | 11/1963 | Di Rito et al. | |
| 3,695,058 A | 10/1972 | Keith, Jr. | |
| 3,734,515 A | 5/1973 | Dudek | |
| 3,759,336 A | 9/1973 | Marcovitz et al. | |
| 4,162,399 A | 7/1979 | Hudson | |
| 4,606,343 A | 8/1986 | Conta et al. | |
| 4,705,038 A | 11/1987 | Sjostrom et al. | |
| 4,722,685 A | 2/1988 | de Estrada et al. | |
| 4,823,807 A | 4/1989 | Russell et al. | |
| 4,874,181 A | 10/1989 | Hsu | |
| 5,129,118 A | 7/1992 | Walmesley | |
| 5,129,570 A | 7/1992 | Schulze et al. | |
| 5,152,744 A | 10/1992 | Krause et al. | |
| 5,301,061 A | 4/1994 | Nakada et al. | |
| 5,312,023 A | 5/1994 | Green et al. | |
| 5,326,013 A | 7/1994 | Green et al. | |
| 5,350,355 A | 9/1994 | Sklar | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,411,508 A | 5/1995 | Bessler et al. | |
| 5,413,267 A | 5/1995 | Solyntjes et al. | |
| 5,427,087 A | 6/1995 | Ito et al. | |
| 5,433,721 A * | 7/1995 | Hooven ............... | A61B 17/068 227/175.1 |
| 5,467,911 A | 11/1995 | Tsuruta et al. | |
| 5,476,379 A | 12/1995 | Disel | |
| 5,487,499 A | 1/1996 | Sorrentino et al. | |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,540,375 A | 7/1996 | Bolanos et al. | |
| 5,540,706 A | 7/1996 | Aust et al. | |
| 5,542,594 A | 8/1996 | McKean et al. | |
| 5,549,637 A | 8/1996 | Crainich | |
| 5,553,675 A | 9/1996 | Pitzen et al. | |
| 5,562,239 A | 10/1996 | Boiarski et al. | |
| 5,564,615 A | 10/1996 | Bishop et al. | |
| 5,609,560 A | 3/1997 | Ichikawa et al. | |
| 5,626,587 A | 5/1997 | Bishop et al. | |
| 5,632,432 A | 5/1997 | Schulze et al. | |
| 5,645,209 A | 7/1997 | Green et al. | |
| 5,647,526 A | 7/1997 | Green et al. | |
| 5,653,374 A | 8/1997 | Young et al. | |
| 5,658,300 A | 8/1997 | Bito et al. | |
| 5,662,662 A | 9/1997 | Bishop et al. | |
| 5,667,517 A | 9/1997 | Hooven | |
| 5,669,918 A * | 9/1997 | Balazs ............... | A61B 17/1155 227/176.1 |
| 5,693,042 A | 12/1997 | Boiarski et al. | |
| 5,704,534 A | 1/1998 | Huitema et al. | |
| 5,713,505 A | 2/1998 | Huitema | |
| 5,762,603 A | 6/1998 | Thompson | |
| 5,779,130 A | 7/1998 | Alesi et al. | |
| 5,782,396 A | 7/1998 | Mastri et al. | |
| 5,782,397 A | 7/1998 | Koukline | |
| 5,792,573 A | 8/1998 | Pitzen et al. | |
| 5,797,536 A | 8/1998 | Smith et al. | |
| 5,820,009 A | 10/1998 | Melling et al. | |
| 5,863,159 A | 1/1999 | Lasko | |
| 5,908,427 A | 6/1999 | McKean et al. | |
| 5,954,259 A | 9/1999 | Viola et al. | |
| 5,964,774 A | 10/1999 | McKean et al. | |
| 5,993,454 A | 11/1999 | Longo | |
| 6,010,054 A | 1/2000 | Johnson et al. | |
| 6,017,354 A | 1/2000 | Culp et al. | |
| 6,032,849 A | 3/2000 | Mastri et al. | |
| 6,045,560 A | 4/2000 | McKean et al. | |
| 6,090,123 A | 7/2000 | Culp et al. | |
| 6,126,651 A | 10/2000 | Mayer | |
| 6,129,547 A | 10/2000 | Cise et al. | |
| 6,165,169 A | 12/2000 | Panescu et al. | |
| 6,239,732 B1 | 5/2001 | Cusey | |
| 6,241,139 B1 | 6/2001 | Milliman et al. | |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,343,731 B1 | 2/2002 | Adams et al. | |
| 6,348,061 B1 | 2/2002 | Whitman | |
| 6,368,324 B1 | 4/2002 | Dinger et al. | |
| 6,371,909 B1 | 4/2002 | Hoeg et al. | |
| 6,434,507 B1 | 8/2002 | Clayton et al. | |
| 6,443,973 B1 * | 9/2002 | Whitman ............ | A61B 17/07207 606/219 |
| 6,461,372 B1 | 10/2002 | Jensen et al. | |
| 6,488,197 B1 | 12/2002 | Whitman | |
| 6,491,201 B1 | 12/2002 | Whitman | |
| 6,533,157 B1 | 3/2003 | Whitman | |
| 6,537,280 B2 | 3/2003 | Dinger et al. | |
| 6,610,066 B2 | 8/2003 | Dinger et al. | |
| 6,611,793 B1 | 8/2003 | Burnside et al. | |
| 6,645,218 B1 | 11/2003 | Cassidy et al. | |
| 6,654,999 B2 | 12/2003 | Stoddard et al. | |
| 6,698,643 B2 | 3/2004 | Whitman | |
| 6,699,177 B1 | 3/2004 | Wang et al. | |
| 6,716,233 B1 | 4/2004 | Whitman | |
| 6,743,240 B2 | 6/2004 | Smith et al. | |
| 6,783,533 B2 | 8/2004 | Green et al. | |
| 6,792,390 B1 | 9/2004 | Burnside et al. | |
| 6,793,652 B1 | 9/2004 | Whitman et al. | |
| 6,817,508 B1 | 11/2004 | Racenet et al. | |
| 6,830,174 B2 | 12/2004 | Hillstead et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,860,892 B1 | 3/2005 | Tanaka et al. | |
| 6,899,538 B2 | 5/2005 | Matoba | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,981,628 B2 | 1/2006 | Wales | |
| 6,981,941 B2 | 1/2006 | Whitman et al. | |
| 6,986,451 B1 | 1/2006 | Mastri et al. | |
| 6,988,649 B2 | 1/2006 | Shelton, IV et al. | |
| 7,032,798 B2 | 4/2006 | Whitman et al. | |
| RE39,152 E | 6/2006 | Aust et al. | |
| 7,055,731 B2 | 6/2006 | Shelton, IV et al. | |
| 7,059,508 B2 | 6/2006 | Shelton, IV et al. | |
| 7,077,856 B2 | 7/2006 | Whitman | |
| 7,111,769 B2 | 9/2006 | Wales et al. | |
| 7,122,029 B2 | 10/2006 | Koop et al. | |

(56) References Cited

U.S. PATENT DOCUMENTS

| | | |
|---|---|---|
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,954,685 B2 * | 6/2011 | Viola ............... A61B 17/07207 227/175.1 |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |

(56) References Cited

U.S. PATENT DOCUMENTS

| | | |
|---|---|---|
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,844,368 B2* | 12/2017 | Boudreaux .......... A61B 17/068 |
| 10,327,779 B2* | 6/2019 | Richard .............. A61B 17/1155 |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1* | 11/2006 | Miyamoto ............ A61B 17/062 606/205 |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1* | 5/2008 | McKenna ........ A61B 17/00491 227/176.1 |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1* | 4/2009 | Zemlok ............ A61B 17/07207 227/175.2 |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1* | 3/2011 | Duval ................ A61B 1/00087 606/1 |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1* | 7/2011 | Ross .................... A61B 17/072 74/89.32 |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1* | 4/2012 | Zemlok ............ A61B 17/07207 606/1 |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0205421 A1* | 8/2012 | Shelton, IV ......... A61B 17/072 227/177.1 |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1* | 10/2012 | Zemlok ................ A61B 17/072 606/1 |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0181035 A1 | 7/2013 | Milliman |
| 2013/0184704 A1* | 7/2013 | Beardsley .............. A61B 18/14 606/41 |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1* | 12/2013 | Nicholas ............ A61B 17/068 606/1 |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299345 A1* | 10/2014 | McRoberts .......... B24B 23/043 173/162.2 |
| 2014/0299647 A1 | 10/2014 | Scirica et al. |
| 2014/0303668 A1 | 10/2014 | Nicholas et al. |
| 2014/0305992 A1* | 10/2014 | Kimsey ................ A61B 17/115 227/176.1 |
| 2014/0358129 A1 | 12/2014 | Zergiebel et al. |
| 2014/0361068 A1 | 12/2014 | Aranyi et al. |

(56) References Cited

U.S. PATENT DOCUMENTS

| | | | |
|---|---|---|---|
| 2014/0365235 A1 | 12/2014 | DeBoer et al. | |
| 2014/0373652 A1 | 12/2014 | Zergiebel et al. | |
| 2015/0014392 A1 | 1/2015 | Williams et al. | |
| 2015/0048144 A1 | 2/2015 | Whitman | |
| 2015/0076205 A1 | 3/2015 | Zergiebel | |
| 2015/0080912 A1 | 3/2015 | Sapre | |
| 2015/0112381 A1 | 4/2015 | Richard | |
| 2015/0122870 A1 | 5/2015 | Zemlok et al. | |
| 2015/0133224 A1 | 5/2015 | Whitman et al. | |
| 2015/0150547 A1 | 6/2015 | Ingmanson et al. | |
| 2015/0150574 A1 | 6/2015 | Richard et al. | |
| 2015/0157320 A1 | 6/2015 | Zergiebel et al. | |
| 2015/0157321 A1 | 6/2015 | Zergiebel et al. | |
| 2015/0164502 A1 | 6/2015 | Richard et al. | |
| 2015/0201931 A1 | 7/2015 | Zergiebel et al. | |
| 2015/0272577 A1 | 10/2015 | Zemlok et al. | |
| 2015/0297199 A1 | 10/2015 | Nicholas et al. | |
| 2015/0303996 A1 | 10/2015 | Calderoni | |
| 2015/0320420 A1 | 11/2015 | Penna et al. | |
| 2015/0320423 A1* | 11/2015 | Aranyi | A61B 17/105 227/177.1 |
| 2015/0327850 A1 | 11/2015 | Kostrzewski | |
| 2015/0342601 A1 | 12/2015 | Williams et al. | |
| 2015/0342603 A1 | 12/2015 | Zergiebel et al. | |
| 2015/0374366 A1 | 12/2015 | Zergiebel et al. | |
| 2015/0374370 A1 | 12/2015 | Zergiebel et al. | |
| 2015/0374371 A1 | 12/2015 | Richard et al. | |
| 2015/0374372 A1 | 12/2015 | Zergiebel et al. | |
| 2015/0374449 A1 | 12/2015 | Chowaniec et al. | |
| 2015/0380187 A1 | 12/2015 | Zergiebel et al. | |
| 2016/0022267 A1* | 1/2016 | Milliman | A61B 17/1155 227/181.1 |
| 2016/0095585 A1 | 4/2016 | Zergiebel et al. | |
| 2016/0095596 A1 | 4/2016 | Scirica et al. | |
| 2016/0106406 A1 | 4/2016 | Cabrera et al. | |
| 2016/0113648 A1 | 4/2016 | Zergiebel et al. | |
| 2016/0113649 A1 | 4/2016 | Zergiebel et al. | |
| 2016/0183938 A1* | 6/2016 | Whitman | A61B 17/07207 227/175.1 |
| 2016/0242779 A1* | 8/2016 | Aranyi | A61B 17/07207 |
| 2016/0249927 A1* | 9/2016 | Beckman | A61B 17/105 227/177.1 |
| 2016/0296234 A1* | 10/2016 | Richard | A61B 17/1155 |
| 2016/0354088 A1* | 12/2016 | Cabrera | A61B 17/1155 |
| 2017/0128123 A1* | 5/2017 | Williams | A61B 18/14 |
| 2017/0281169 A1* | 10/2017 | Harris | A61B 17/1155 |
| 2017/0281184 A1* | 10/2017 | Shelton, IV | A61B 17/00234 |
| 2020/0008802 A1* | 1/2020 | Aronhalt | A61B 17/07207 |

FOREIGN PATENT DOCUMENTS

| | | | |
|---|---|---|---|
| CN | 1957854 A | 5/2007 | |
| CN | 101495046 A | 7/2009 | |
| CN | 102247182 A | 11/2011 | |
| DE | 102008053842 A1 | 5/2010 | |
| EP | 0705571 A1 | 4/1996 | |
| EP | 1563793 A1 | 8/2005 | |
| EP | 1769754 A1 | 4/2007 | |
| EP | 2316345 A1 | 5/2011 | |
| EP | 2668910 A2 | 12/2013 | |
| ES | 2333509 A1 | 2/2010 | |
| JP | 2005-125075 A | 5/2005 | |
| KR | 20120022521 A | 3/2012 | |
| WO | 2011/108840 A2 | 9/2011 | |
| WO | 2012/040984 A1 | 4/2012 | |

OTHER PUBLICATIONS

Extended European Search Report corresponding to counterpart International Application No. EP 14 18 4882.0 dated May 12, 2015.
Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 9783.3 dated Sep. 3, 2015.
Extended European Search Report corresponding to counterpart International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.

(56) References Cited

OTHER PUBLICATIONS

Australian Examination Report No. 1 corresponding to International Application No. AU 2013205872 dated Oct. 19, 2016.
Australian Examination Report from Appl. No. AU 2013205840 dated Nov. 3, 2016.
European Search Report corresponding to EP 15 184 915.5-1654 dated Sep. 16, 2016.

* cited by examiner

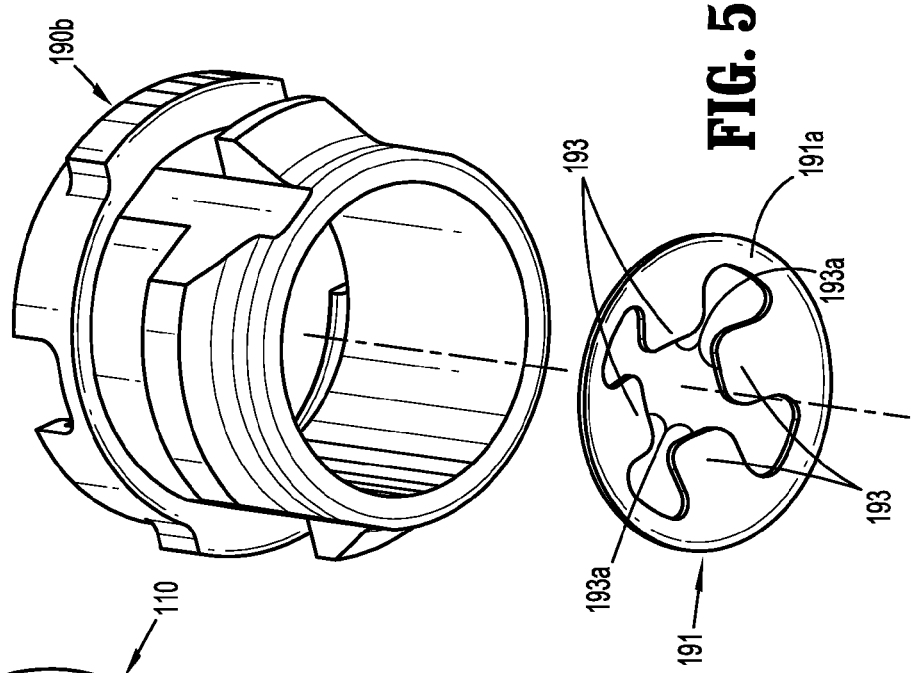
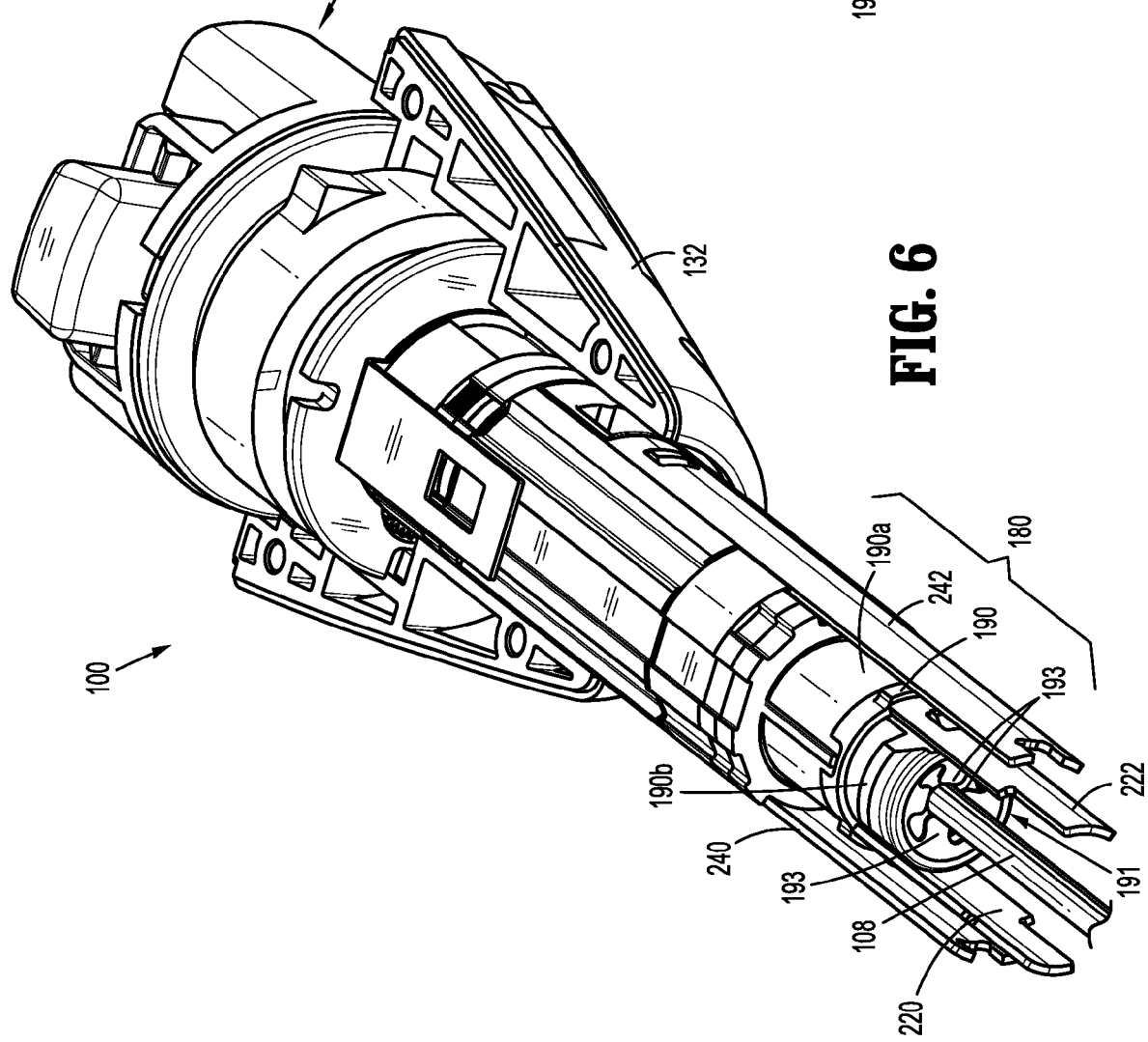

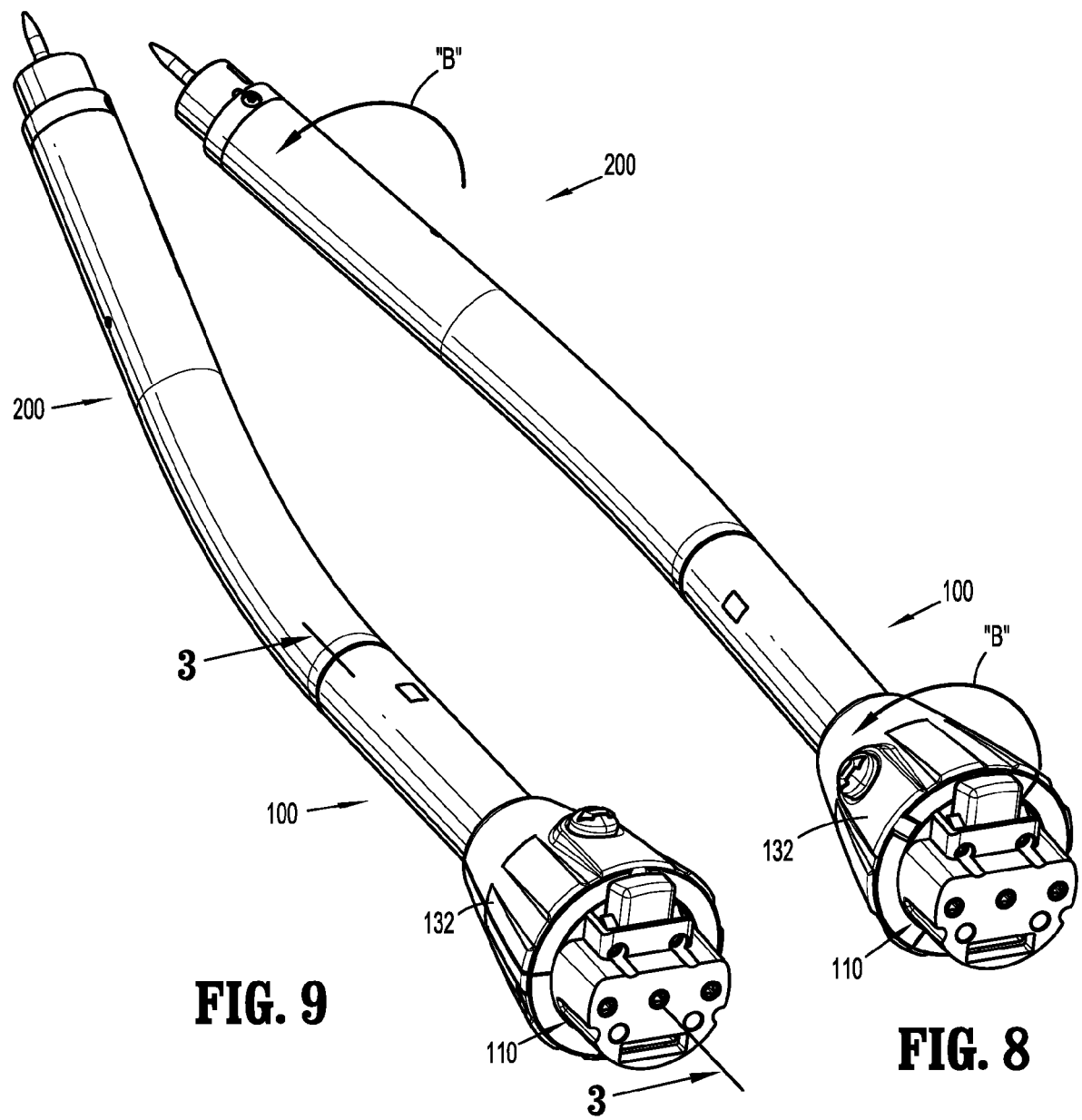

BRAKE FOR ADAPTER ASSEMBLIES FOR SURGICAL DEVICES

CROSS-REFERENCE TO RELATED APPLICATIONS

This application claims the benefit of and priority to U.S. Provisional Patent Application Ser. No. 62/334,013, filed May 10, 2016, the entire disclosure of which is incorporated by reference herein.

BACKGROUND

Technical Field

The present disclosure relates to adapter and extension assemblies for selectively connecting tool assemblies to actuation units of powered surgical devices. More specifically, the present disclosure relates to a brake member for preventing rotation of a drive assembly in the adapter assemblies.

Background of Related Art

Powered devices for use in surgical procedures are known. To permit reuse of the handle assemblies of these powered surgical devices and so that the handle assembly may be used with a variety of end effectors, adapter assemblies and extension assemblies have been developed for selective attachment to the handle assemblies and to a variety of end effectors. Following use, the adapter and/or extension assemblies may be disposed of along with the end effector. In some instances, the adapter assemblies and extension assemblies may be sterilized for reuse.

The adapter assemblies are configured to permit rotation of actuation units relative to the adapter assemblies. When the actuation units are rotated relative to the adapter assemblies, the free wheel or back drive of the motors in the actuation units require more torque than the free turning or advancing of the drive members within the adapter assemblies, resulting in movement of drive members within the adapter assemblies. Movement of the drive members within the adapter assemblies may effect of the calibration the drive members within the adapter assembly.

To maintain calibration of the drive members within the adapter assemblies, it would be beneficial to provide a brake to prevent rotation of the drive member within the adapter assembly as the adapter assembly is rotated relative to the handle assembly.

SUMMARY

An adapter assembly for operably connecting an end effector to an electrosurgical instrument is provided. The adapter assembly includes a drive transfer assembly, a drive member, and a first pusher assembly. The drive transfer assembly includes first and second rotatable shafts. The drive member is operably connected to the first rotatable shaft for transferring rotational motion from the first rotatable shaft to effect a first function and the first pusher assembly is operably connected to the second rotatable shaft for converting rotational motion from the second rotatable shaft to longitudinal movement to effect a second function. The first pusher assembly includes a brake member for rotationally locking the drive member relative to the first pusher assembly.

In embodiments, the adapter assembly may further include a second pusher assembly and the drive transfer assembly may include a third rotatable shaft. The second pusher assembly may be operably connected to the third rotatable shaft for converting rotational motion from the third rotatable shaft to longitudinal movement to effect a third function. The adapter assembly may further include an extension assembly having a flexible band assembly operably connected to the first pusher assembly. The first pusher assembly may include a planetary gear assembly. The first pusher assembly may include a drive screw operably connected to the planetary gear assembly. The first pusher assembly includes a pusher member operably received about the first drive screw. Rotation of the drive screw may cause longitudinal movement of the pusher member.

In embodiments, the brake member may be disposed within the pusher member. The brake member may include a collet having a plurality of leaves. The plurality of leaves may extend radially inward. The plurality of leaves extend proximally. The plurality of leaves of the collet may engage the drive member. The drive member may extend through the collet. The drive member may define a longitudinal axis and the collet may define a plane extending perpendicular to the longitudinal axis.

Also provided is a surgical stapling device including an electromechanical surgical instrument, an end effector, and an adapter assembly for operably connecting the end effector to the electromechanical surgical instrument. The adapter assembly includes a drive member for transferring rotational motion from a first rotatable shaft to effect a first function, and a first pusher assembly for converting rotational motion from a second rotatable shaft to longitudinal movement to effect a second function. The first pusher assembly includes a brake member for rotationally locking the drive member relative to the first pusher assembly.

BRIEF DESCRIPTION OF THE DRAWINGS

Embodiments of the present disclosure are described herein with reference to the accompanying drawings, wherein:

FIG. 5 is a perspective end view of a distal portion of a pusher member and a brake member of a pusher assembly of the adapter assembly of FIGS. 1-4, with parts separated;

FIG. 6 is perspective distal side view of the adapter assembly of FIGS. 1-4, with an outer sleeve and an upper half-section of a rotation handle of a rotation handle assembly of the adapter assembly removed;

FIG. 8 is an enlarged, perspective view of a coupling assembly and a transfer assembly of the adapter assembly of FIGS. 2-7; and FIG. 9 is a perspective end view of the adapter assembly of FIGS. 1-4 with the outer sleeve and rotatable handle in a first orientation relative to the coupling assembly.

DETAILED DESCRIPTION OF EMBODIMENTS

Figure 1:
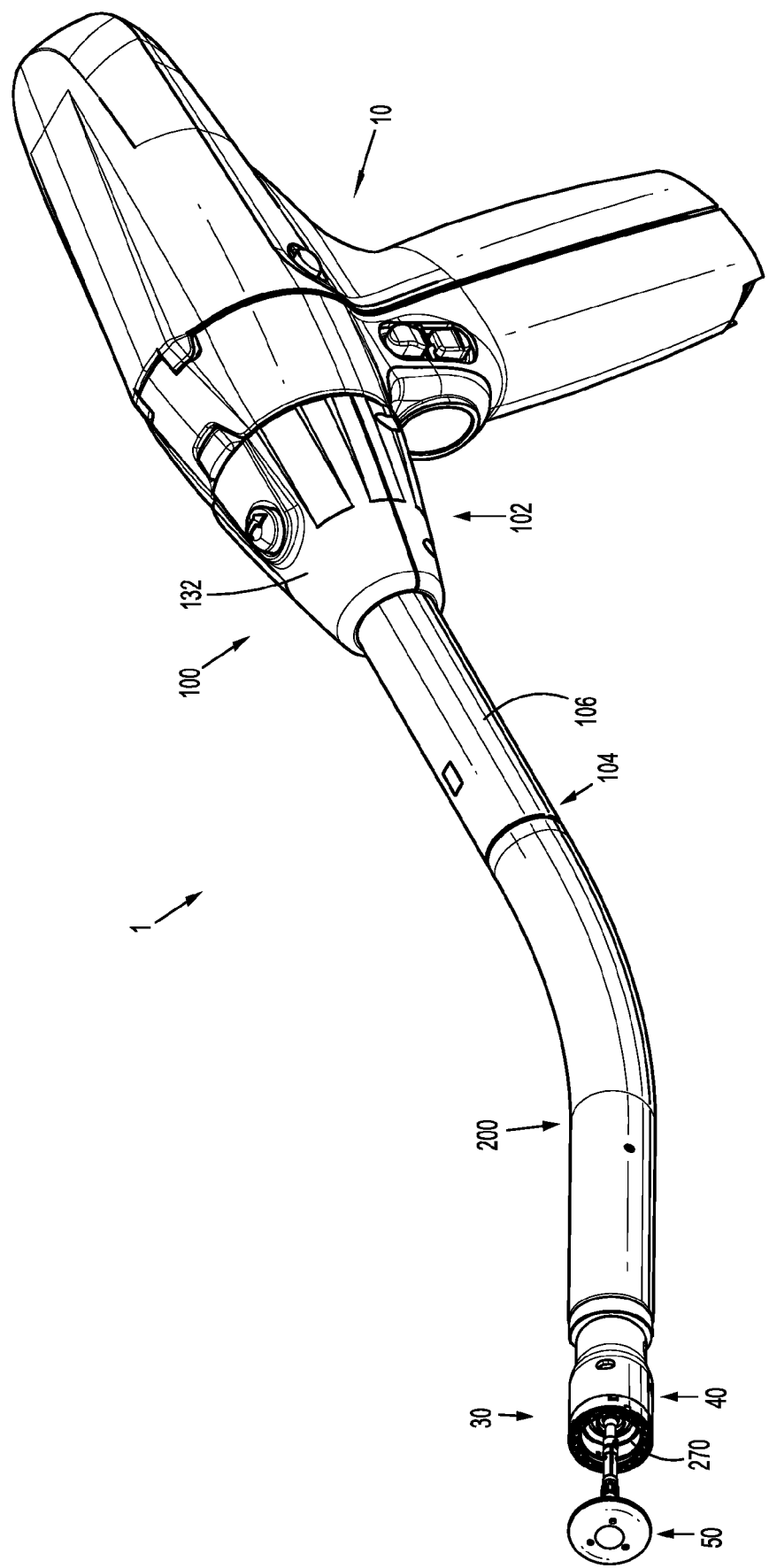
FIG. 1 is a perspective view of an adapter assembly, in accordance with an embodiment of the present disclosure, an exemplary extension assembly, an exemplary tool assembly, and an exemplary electromechanical surgical device.

Embodiments of the presently disclosed adapter assemblies for surgical devices and/or actuation units are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

With reference to FIG. 1, an adapter assembly in accordance with an embodiment of the present disclosure, shown generally as the adapter assembly 100 configured for selective connection to a powered hand held electromechanical instrument shown, generally as actuation unit 10, and for connection with an extension assembly 200. As illustrated in FIG. 1, the actuation unit 10 is configured for releasable connection with the adapter assembly 100, and, in turn, the adapter assembly 100 is configured for releasable connection with the extension assembly 200. Alternatively, the adapter assembly 100 and the extension assembly 200 may be integrally formed. The extension assembly 200 is configured for selective connection with a tool assembly or end effector, e.g. tool assembly 30, including, in the illustrative embodiment shown, a loading unit, e.g. loading unit 40, and an anvil assembly, e.g., anvil assembly 50, for applying a circular array of staples (not shown) to tissue (not shown).

The actuation unit 10, the adapter assembly 100, the extension assembly 200 and the tool assembly 30 are collectively referred to as the surgical stapling device 1. Although the embodiments of the present disclosure will be discussed as relates to a surgical stapling device, it is envisioned that the aspects of the present disclosure may be modified for various surgical devices.

The actuation unit 10 and the extension assembly 200 will only be described in detail to the extent necessary to fully disclose the aspects of the present disclosure. For a detailed description of the structure and function of an exemplary actuation unit, please refer to commonly owned U.S. Pat. No. 9,055,943 ("the '943 patent"), the content of which is incorporated by reference herein in its entirety. For a detailed description of the structure and function of an exemplary extension assembly, please refer to commonly owned U.S. patent application Ser. No. 14/875,766 ("the '766 application"), filed Oct. 6, 2015, the content of which is incorporated by reference herein in its entirety.

Figure 2:
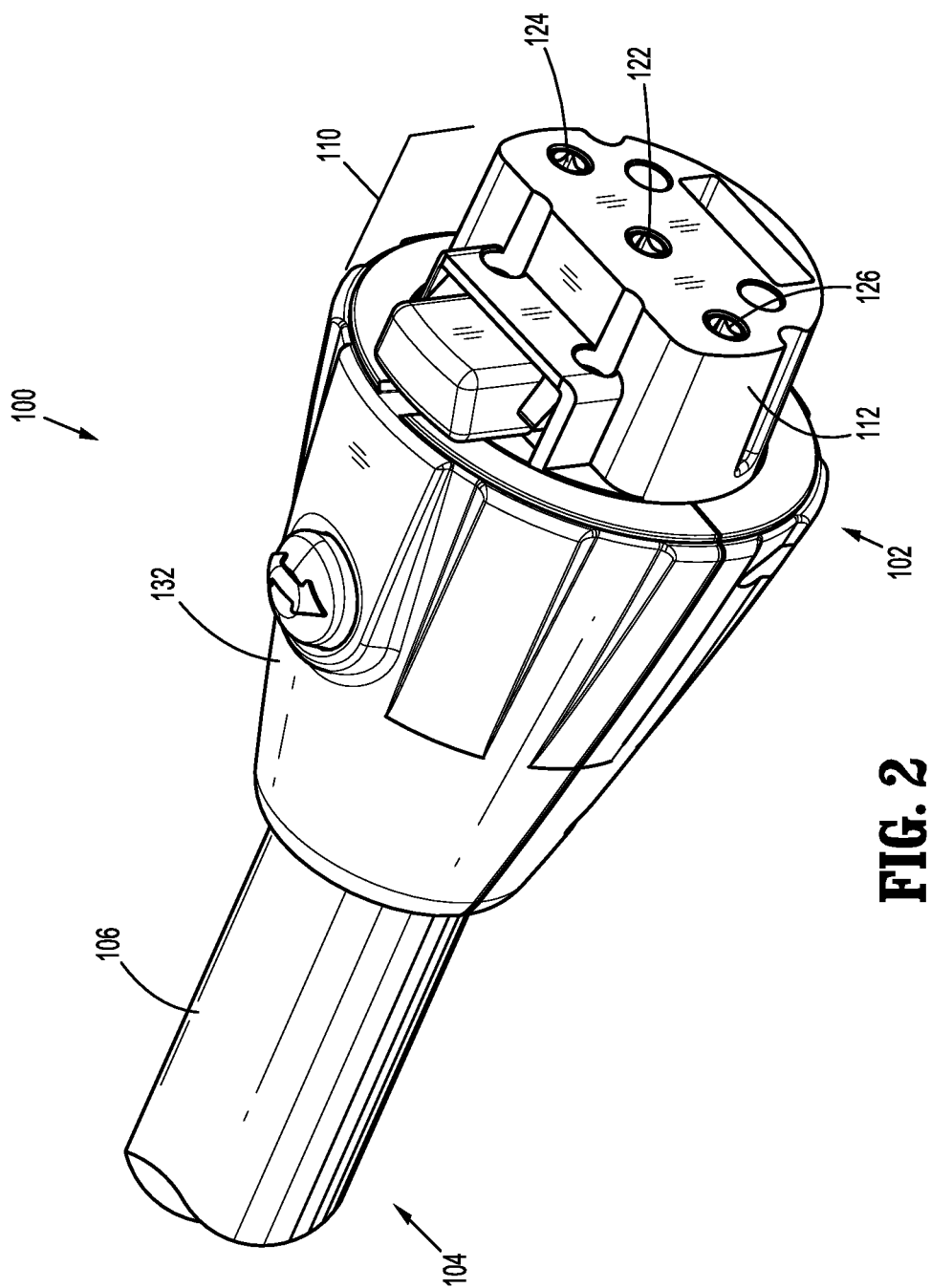
FIG. 2 is a perspective side view of a proximal end of the adapter assembly of FIG. 1.
Figure 3:
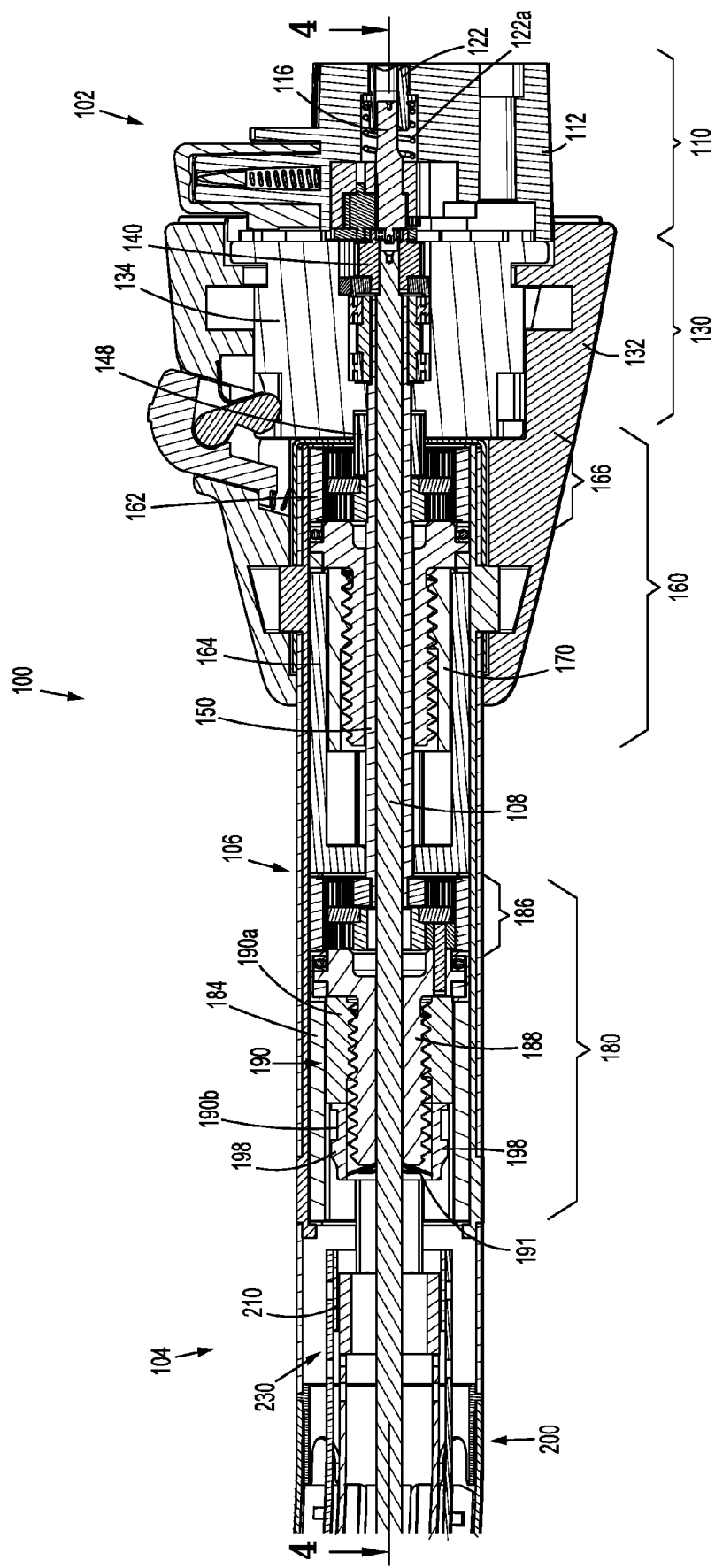
FIG. 3 is a cross-sectional side view of the adapter assembly of FIGS. 1 and 2, taken along line 3-3 in FIG. 9.
Figure 4:
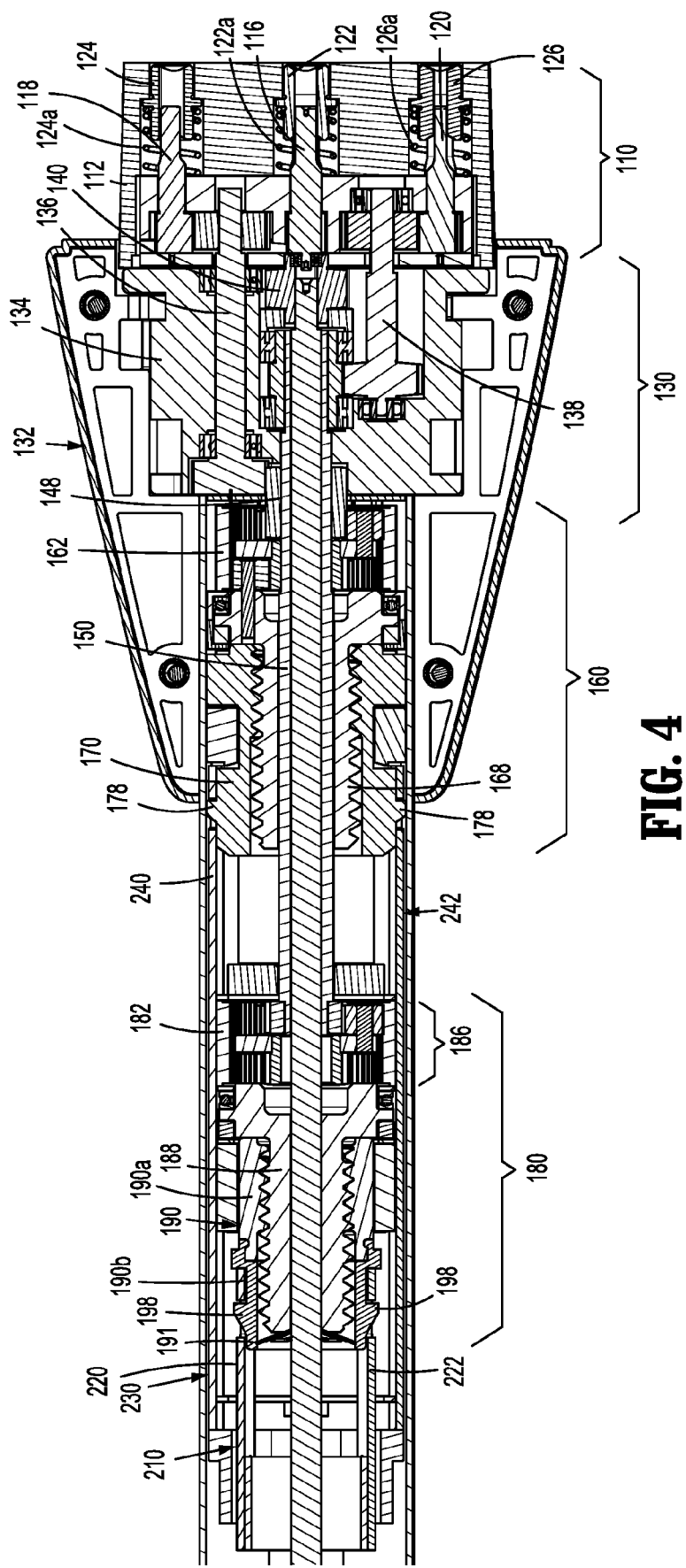
FIG. 4 is a cross-sectional side view of the adapter assembly of FIGS. 1 and 2, taken along line 4-4 in FIG. 3.

With additional reference to FIGS. 2-4, the adapter assembly 100 includes a proximal end portion 102 configured for operable connection to the actuation unit 10 (FIG. 1) and a distal end portion 104 configured for operable connection to the extension assembly 200 (FIG. 1). From the proximal end portion 102 to the distal end portion 104, the adapter assembly 100 includes a drive coupling assembly 110, a drive transfer assembly 130 operably connected to the drive coupling assembly 110, a first pusher assembly 160 operably connected to the drive transfer assembly 130, and a second pusher assembly 180 operably connected to the drive transfer assembly 130. The first pusher assembly 160 and the second pusher assembly 180 are operably maintained within an outer sleeve 106. As will be described in further detail below, a drive shaft 108 extends longitudinally through the adapter assembly 100 and is operably connected to the drive transfer assembly 130.

The drive coupling assembly 110 is configured to releasably secure the adapter assembly 100 to the actuation unit 10 (FIG. 1). The drive coupling assembly 110 includes first, second, and third rotatable proximal drive shafts 116, 118, 120 and respective first, second, and third connector sleeves 122, 124, 126 rotatably supported within a connector housing 112. Each of the first, second, and third connector sleeves 122, 124, 126 is configured to mate with respective first, second, and third drive connectors (not shown) of actuation unit 10 (FIG. 1).

The drive coupling assembly 110 also includes first, second and third biasing members 122a, 124a and 126a disposed distally of the respective first, second and third connector sleeves 122, 124, 126 to help maintain the connector sleeves 122, 124, and 126, respectively, engaged with the distal end of the respective drive rotatable drive connectors (not shown) of the actuation unit 10 when the adapter assembly 100 is connected to the actuation unit 10. For a detailed description of an exemplary drive coupling assembly, please refer to the '766 application, the contents of which were previously incorporated herein by reference.

With continued reference to FIGS. 3 and 4, the drive transfer assembly 130 operably connects distal ends of first, second and third rotatable proximal drive shafts 116, 118 and 120 to drive shaft 108, first pusher assembly 160, and second pusher assembly 180, respectively. The drive transfer assembly 130 includes a drive transfer housing 134 secured to the connector housing 112 of the drive coupling assembly 110. The drive transfer housing 134 operates to rotatably support first and second rotatable distal drive shafts 136, 138 and a drive member 140 therein and rotatably support a rotation handle assembly 132 thereabout. The rotation handle assembly 132 is securely affixed to the outer sleeve 106 of the adapter assembly 100 and facilitates selective rotation of the outer sleeve 106, and the attached extension assembly 200 (FIG. 1) and tool assembly 30 (FIG. 1). For a detailed description of an exemplary rotation handle assembly, please refer to commonly owned U.S. Pro. Pat. App. Ser. No. 62/333,976 filed May 10, 2016, the content of which is incorporated by reference herein in its entirety.

The drive transfer assembly 130 also includes a drive connector 148 (FIG. 3) operably connecting the first rotatable distal drive shaft 136 to the first pusher assembly 160 and a tubular connector 150 operably connecting the second rotatable distal drive shaft 138 to the second pusher assembly 180.

The first pusher assembly 160 includes proximal and distal housing sections 162, 164 (FIG. 3), a planetary gear assembly 166 operably mounted within the proximal housing section 162, a screw member 168 operably connected to the planetary gear assembly 166 and rotatably supported within the distal housing section 164, and a pusher member 170 operably connecting screw member 168 and slidably disposed within distal housing section 164. The first pusher assembly 160 will only be described to the extent necessary to disclose the aspects of the present disclosure. For a detailed description of the operation and function of an exemplary pusher assembly, including an exemplary planetary gear assembly, please refer to the '766 application, the contents of which were previously incorporated herein in its entirety.

The screw member 168 of the first pusher assembly 160 is rotatably supported within proximal housing portion 162 and operably engages the pusher member 170. Operation of the planetary gear assembly 166 rotates the screw member 168. As screw member 168 is rotated in a first direction, the pusher member 170 is moved in a proximal direction and when the screw member 168 is rotated in a second direction, the pusher member 170 is moved in a distal direction. The pusher member 170 operably engages the screw member 168 and includes a pair of tabs 178 for engaging connector extensions 240, 242 (FIG. 4) of outer flexible band assembly 230 (FIG. 4) of extension assembly 200 (FIG. 1).

The second pusher assembly 180 is substantially similar to first pusher assembly 160, and includes proximal and distal housing sections 182, 184 (FIG. 3), a planetary gear assembly 186 operably mounted within the proximal housing section 182, a screw member 188 operably connected to the planetary gear assembly 186 and rotatably supported within the distal housing section 184, and a pusher assembly 190 operably connected to the screw member 188 and slidably disposed within the distal housing section 184.

The screw member 188 is rotatably supported within the proximal housing portion 182 and operably engages the pusher assembly 190. Operation of the planetary gear assembly 186 rotates the screw member 188. As the screw member 188 is rotated in a first direction, the pusher assembly 190 is moved in a distal direction, and when the screw member 188 is rotated in a second direction, the pusher assembly 190 is moved in a proximal direction.

The pusher member 190 includes a proximal portion 190a configured to operably engage the screw member 188, and a distal portion or nut portion 190b for operably engaging the extension assembly 200. More particularly, the proximal portion 190b of the pusher member 190 includes a pair of tabs 198 for engaging connector extensions 220, 222 (FIG. 4) of inner flexible band assembly 210 (FIG. 4) of extension assembly 200 (FIG. 1). Although shown as separate components, it is envisioned that the proximal and distal portions 190a, 190b of the pusher member 190 may be integrally formed, e.g., monolithic.

With additional reference now to FIGS. 5 and 6, the pusher member 190 of the second pusher assembly 180 further includes a brake member, e.g., collet or Belleville washer spring 191. The collet 191 includes an outer ring 191a and a plurality of leaves 193 extending radially inwardly from the outer ring 191a and in a proximal direction (when mounted to the pusher member 190). Although shown including four (4) leaves 193, it is envisioned that the collet 191 can include any number of leaves 193. Each of the plurality of leaves 193 extend radially inward and proximally. The collet 191 is secured within the distal portion 190b of the pusher member 190 using welding, adhesive, or in any manner suitable for maintaining the collet 191 rotationally fixed relative to the pusher member 190.

Figure 7:
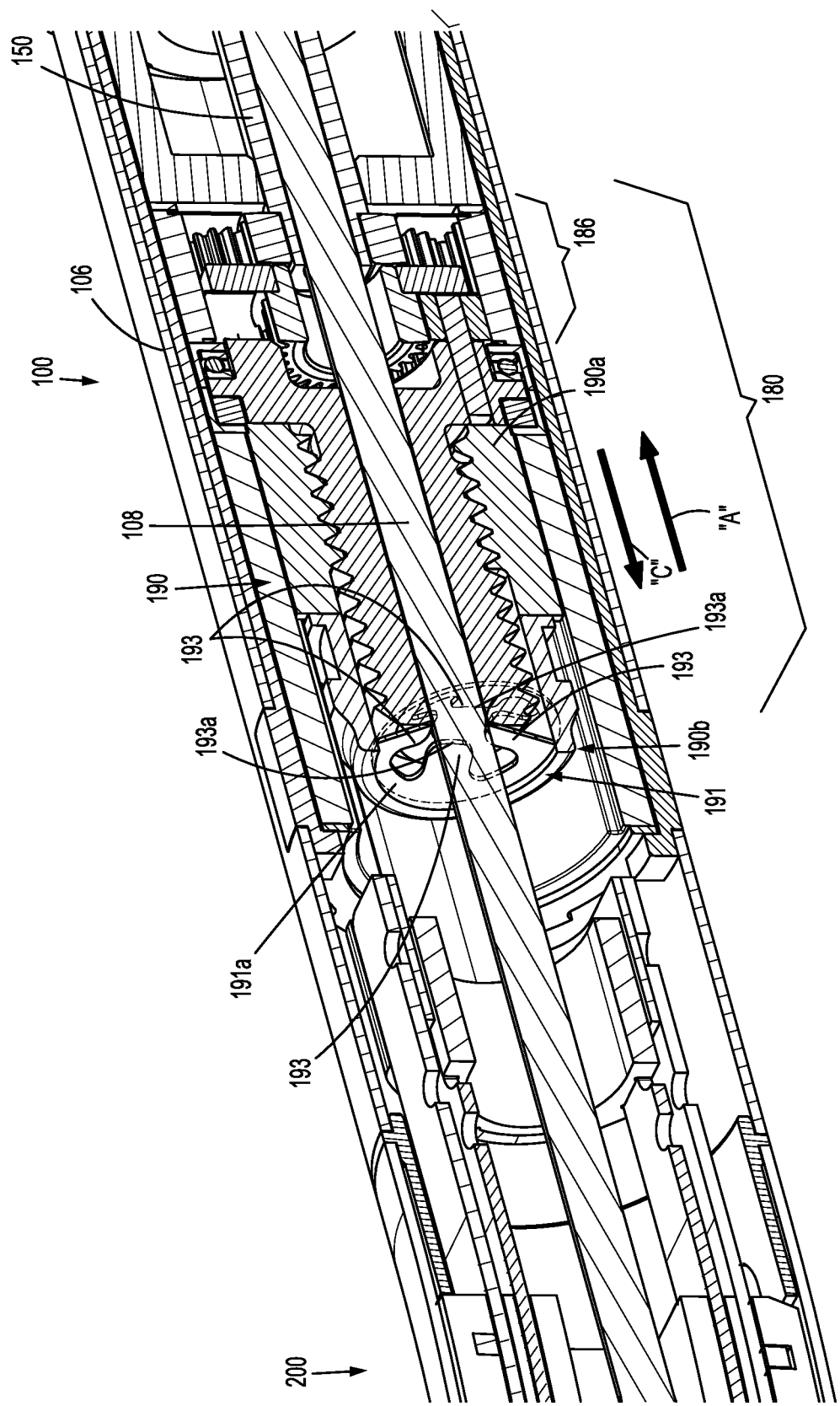
FIG. 7 is a cross-sectional perspective side view of a distal portion of the adapter assembly of FIGS. 1-4.

Each of the leaves 193 of the collet 191 include free ends 193a configured to engage the drive shaft 108 when the pusher member 190 of the second pusher assembly 180 is moved in a proximal direction, as indicated by arrow "A" in FIG. 7. Engagement of the free ends 193a of the leaves 193 with the drive shaft 108 prevents the drive shaft 108 from rotating relative to the pusher member 190 during rotation of the actuation unit 10 relative to the adapter assembly 100. In this manner, when the leaves 193 of the collet 191 engage the drive shaft 108, the drive shaft 108 is rotationally fixed relative to the pusher member 190 such that the drive shaft 108 back drives the first drive connector (not shown) of the actuation unit 10 as the actuation unit 10 is rotated relative to the adapter assembly 100.

Conversely, the free ends 193a of the leaves 193 of the collet 191 disengage from the drive shaft 108 when the pusher member 190 is moved in a distal direction, as indicated by arrow "C" in FIG. 7, to unlock the drive shaft 108 and permit rotation of the drive shaft 108 relative to the pusher member 190. It is envisioned that the drive shaft 108 may include flattened sides to facilitate engagement of the leaves 193 of the collet 191 with the drive shaft 108.

Although the brake member of the present disclosure is shown and described as being a component of the second pusher assembly 180 of the adapter assembly 100, it is envisioned that the brake member may instead, or additionally, be incorporated into the first pusher assembly 160 of the adapter assembly 100.

As noted above, the extension assembly 200 operably connects the adapter assembly 100 with the tool assembly 30. More particularly, the extension assembly 200 includes a trocar assembly 270 (FIG. 1) operably connected to the drive shaft 108 for advancing and retracting, for example, the anvil assembly 50 (FIG. 1) relative to the loading unit 40 (FIG. 1), to clamp tissue (not shown). The inner flexible band assembly 210 (FIG. 4) of the extension assembly 200 is operably connected to the pusher member 190 of the second pusher assembly 180 for advancing and retracting, for example, a staple pusher (not shown) of the loading unit 40, to staple tissue (not shown), and the outer flexible band assembly 230 (FIG. 4) is operably connected to the pusher member 170 of the first pusher assembly 160 for advancing and retracting, for example, a knife pusher (not shown) of the loading unit 40, to cut tissue (not shown). For a detailed description of the function and operation of an exemplary extension assembly, please refer to the '766 application.

The operation of the adapter assembly 100, and more particularly the brake member 191, will now be described with reference to FIGS. 7-9. After the extension assembly 200 is secured to adapter assembly 100, the adapter assembly 100 is secured to the actuation unit 10 (FIG. 1), and the loading unit 40 (FIG. 1) of tool assembly 30 (FIG. 1) is secured to the extension assembly 200, the adapter assembly 100 and the extension assembly 200 are used to position the loading unit 40 within the patient (not shown) in a traditional manner. Depending on the procedure being performed, the anvil assembly 50 (FIG. 1) of the tool assembly 30 may be secured to the trocar assembly 270 of the extension assembly 200 prior to or subsequent the positioning of the loading unit 40 within the patient.

During positioning and operation of the surgical stapling device 1 (FIG. 1), it may be necessary to rotationally orient the actuation unit 10 relative to the adapter assembly 100 to, for example, accommodate the limitations in space in the operating room, and/or for ease of use by the clinician. In order to maintain calibration of the adapter assembly 100, the extension assembly 200, and/or the tool assembly 30 (FIG. 1), the drive shaft 108 of the adapter assembly 100 is rotationally locked relative to the adapter assembly 100 as the actuation unit 10 (FIG. 1) and the adapter assembly 100 are rotated relative to one another other such that the drive shaft 108 back drives the first drive connector (not shown) of the actuation unit 10.

With particular reference to FIG. 7, prior to rotating the actuation unit 10 relative to the adapter assembly 100, the actuation unit 10 is activated to cause the pusher member 190 of the second pusher assembly 180 to move proximally, i.e., retract, as indicated by arrow "A". More particularly, the third drive connector (not shown) of the actuation unit 10 rotates third proximal drive shaft 120 (FIG. 4) of the coupling assembly 110 (FIG. 4), which rotates the second distal drive shaft 138 (FIG. 4) of the drive transfer assembly 130 (FIG. 4), which rotates the tubular connector 150 (FIG. 4) of the drive transfer assembly 130, which drives the planetary gear system 186 of the second pusher assembly 180, which causes rotation of the screw member 188, and subsequent retraction of the pusher member 190 of the second pusher assembly 180.

With continued reference to FIG. 7, retraction of the pusher member 190 of the second pusher assembly 180 causes the free ends 193*a* of the leaves 193 of the collet 191 of the second pusher assembly 180 to engage the drive shaft 108 extending through the adapter assembly 100. Engagement of the collet 191 with the drive shaft 108 rotationally locks or fixes the drive shaft 108 relative to the pusher member 190, thereby rotationally fixing the drive shaft 108 within the outer sleeve 106 of the adapter assembly 100.

It is envisioned that the adapter assembly 100 may be provided to the clinician with the pusher member 190 of the second pusher assembly 180 in the proximal position, and thus, with the drive shaft 108 already rotationally fixed.

Once the drive shaft 108 is rotationally fixed relative to the adapter assembly 100, the actuation unit 10 (FIG. 1), including the coupling assembly 110 of the adapter assembly 100, and the rotation handle 132 (FIG. 1) and outer sleeve 108 of the adapter assembly 100 may be rotated relative to one another while the calibration of the tool assembly 30 (FIG. 1) is maintained. As actuation unit 10 is rotated relative to the adapter assembly 100, the rotationally locked or fixed condition of the drive shaft 108 results in the first drive connector (not shown) of the actuation unit 10 back driving a motor (not shown) connected to the first drive connector (not shown).

Following rotation of the actuation unit 10 (FIG. 1) and the adapter assembly 100 relative to one another, the actuation unit 10 is activated to cause the pusher member 190 of the second pusher assembly 180 to move distally, e.g., advance, as indicated by arrow "C" in FIG. 7. Advancement of the pusher member 190 of the second pusher assembly 180 causes the leaves 193 of the collet 191 to disengage from the drive shaft 108. Once the leaves 193 of the collet 191 are disengaged from the drive shaft 108, the drive shaft 108 is free to rotate and the adapter assembly 100 operates in a traditional manner.

For a detailed description of the operation of an exemplary adapter assembly, extension assembly, and tool assembly, please refer to the '766 application Any of the components described herein may be fabricated from either metals, plastics, resins, composites or the like taking into consideration strength, durability, wearability, weight, resistance to corrosion, ease of manufacturing, cost of manufacturing, and the like.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An adapter assembly for operably connecting an end effector to an electromechanical surgical instrument, the adapter assembly comprising:
    a drive transfer assembly including a first rotatable shaft, a second rotatable shaft laterally spaced from the first rotatable shaft, and a third rotatable shaft;
    a drive member operably connected to the first rotatable shaft for transferring rotational motion from the first rotatable shaft to effect a first function;
    a first pusher assembly operably connected to the second rotatable shaft for converting rotational motion from the second rotatable shaft to longitudinal movement to effect a second function, the first pusher assembly including a brake member for rotationally locking the drive member relative to the first pusher assembly; and
    a second pusher assembly operably connected to the third rotatable shaft for converting rotational motion from the third rotatable shaft to longitudinal movement to effect a third function.

2. An adapter assembly for operably connecting an end effector to an electromechanical surgical instrument, the adapter assembly comprising:
    a drive transfer assembly including a first rotatable shaft and a second rotatable shaft laterally spaced from the first rotatable shaft;
    a drive member operably connected to the first rotatable shaft for transferring rotational motion from the first rotatable shaft to effect a first function;
    a first pusher assembly operably connected to the second rotatable shaft for converting rotational motion from the second rotatable shaft to longitudinal movement to effect a second function, the first pusher assembly including a brake member for rotationally locking the drive member relative to the first pusher assembly; and
    an extension assembly including at least one flexible band assembly operably connected to the first pusher assembly.

3. An adapter assembly for operably connecting an end effector to an electromechanical surgical instrument, the adapter assembly comprising:
    a drive transfer assembly including a first rotatable shaft and a second rotatable shaft laterally spaced from the first rotatable shaft;
    a drive member operably connected to the first rotatable shaft for transferring rotational motion from the first rotatable shaft to effect a first function; and
    a first pusher assembly operably connected to the second rotatable shaft for converting rotational motion from the second rotatable shaft to longitudinal movement to effect a second function, the first pusher assembly including a brake member for rotationally locking the drive member relative to the first pusher assembly, wherein the first pusher assembly includes a planetary gear assembly.

4. The adapter assembly of claim 3, wherein the first pusher assembly includes a first drive screw operably connected to the planetary gear assembly.

5. The adapter assembly of claim 4, wherein the first pusher assembly includes a pusher member operably received about the first drive screw.

6. The adapter assembly of claim 5, wherein rotation of the first drive screw causes longitudinal movement of the pusher member.

7. The adapter assembly of claim 5, wherein the brake member is disposed within the pusher member.

8. An adapter assembly for operably connecting an end effector to an electromechanical surgical instrument, the adapter assembly comprising:
    a drive transfer assembly including a first rotatable shaft and a second rotatable shaft laterally spaced from the first rotatable shaft;

a drive member operably connected to the first rotatable shaft for transferring rotational motion from the first rotatable shaft to effect a first function; and a first pusher assembly operably connected to the second rotatable shaft for converting rotational motion from the second rotatable shaft to longitudinal movement to effect a second function, the first pusher assembly including a brake member for rotationally locking the drive member relative to the first pusher assembly, wherein the brake member includes a collet having a plurality of leaves.

9. The adapter assembly of claim 8, wherein the plurality of leaves of the collet extend radially inward.

10. The adapter assembly of claim 8, wherein the plurality of leaves of the collet extend proximally.

11. The adapter assembly of claim 8, wherein the plurality of leaves of the collet engage the drive member.

12. The adapter assembly of claim 8, wherein the drive member extends through the collet.

13. The adapter assembly of claim 8, wherein the drive member defines a longitudinal axis and the collet defines a plane extending perpendicular to the longitudinal axis.

14. A surgical stapling device comprising:
an electromechanical surgical instrument;
an end effector; and
an adapter assembly for operably connecting the end effector to the electromechanical surgical instrument, the adapter assembly defining a longitudinal axis and including:
a drive member for transferring rotational motion from a first rotatable shaft to effect a first function; and
a first pusher assembly for converting rotational motion from a second rotatable shaft to longitudinal movement to effect a second function, the first pusher assembly including a brake member for rotationally locking the drive member relative to the first pusher assembly, the first and second rotatable shafts extending parallel to the longitudinal axis of the adapter assembly, wherein the brake member includes a collet having a plurality of leaves.

15. The surgical stapling device of claim 14, wherein the plurality of leaves of the collet extend radially inward.

16. The surgical stapling device of claim 14, wherein the plurality of leaves of the collet extend proximally.

17. The surgical stapling device of claim 14, wherein the plurality of leaves of the collet engage the drive member.

18. The surgical stapling device of claim 14, wherein the drive member extends through the collet.

19. An adapter assembly for operably connecting an end effector to an electromechanical surgical instrument, the adapter assembly comprising:
a drive member for transferring rotational motion, the drive member being configured to effect a first function; and
a pusher assembly operably disposed about the drive member for converting rotational motion to longitudinal movement to effect a second function, the pusher assembly including a brake member for rotationally locking the drive member relative to the pusher assembly, the brake member including a collet having a plurality of leaves.

* * * * *